US008449896B2

(12) United States Patent
Kamada et al.

(10) Patent No.: US 8,449,896 B2
(45) Date of Patent: May 28, 2013

(54) PHARMACEUTICAL COMPOSITION HAVING IMPROVED SOLUBILITY

(75) Inventors: Makoto Kamada, Hiratsuka (JP); Motonori Kidokoro, Hiratsuka (JP); Gaku Sekiguchi, Hiratsuka (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/328,847

(22) Filed: Dec. 16, 2011

(65) Prior Publication Data

US 2012/0114711 A1 May 10, 2012

Related U.S. Application Data

(63) Continuation of application No. PCT/JP2010/060261, filed on Jun. 17, 2010.

(30) Foreign Application Priority Data

Jun. 18, 2009 (JP) ................................. 2009-145112

(51) Int. Cl.
*A61K 9/14* (2006.01)
*A61K 9/20* (2006.01)

(52) U.S. Cl.
USPC ............ 424/400; 977/773; 977/906; 977/915

(58) Field of Classification Search
USPC ........................... 424/400; 977/773, 906, 915
See application file for complete search history.

(56) References Cited

U.S. PATENT DOCUMENTS

| | | | |
|---|---|---|---|
| 5,055,600 A | 10/1991 | Wagner | |
| 5,149,855 A | 9/1992 | Sakimae et al. | |
| 5,677,469 A | 10/1997 | van Eikeren et al. | |
| 7,192,968 B2 | 3/2007 | Yoshino et al. | |
| 7,342,014 B2 | 3/2008 | Ohta et al. | |
| 7,365,205 B2 | 4/2008 | Ohta et al. | |
| 7,576,135 B2 | 8/2009 | Ohta et al. | |
| 7,674,904 B2 | 3/2010 | Doshan et al. | |
| 2004/0122063 A1 | 6/2004 | Yoshino et al. | |
| 2005/0020645 A1 | 1/2005 | Ohta et al. | |
| 2005/0119486 A1 | 6/2005 | Ohta et al. | |
| 2005/0245565 A1 | 11/2005 | Ohta et al. | |
| 2006/0252837 A1 | 11/2006 | Ohta et al. | |
| 2006/0275357 A1* | 12/2006 | Oomura et al. ............... | 424/451 |
| 2007/0135476 A1 | 6/2007 | Nagasawa et al. | |
| 2008/0015215 A1 | 1/2008 | Ohta et al. | |
| 2009/0105491 A1 | 4/2009 | Sato et al. | |
| 2009/0192313 A1 | 7/2009 | Nagasawa et al. | |
| 2009/0270446 A1 | 10/2009 | Ohta et al. | |
| 2009/0281074 A1 | 11/2009 | Ohta et al. | |
| 2010/0081685 A1 | 4/2010 | Kojima et al. | |

FOREIGN PATENT DOCUMENTS

| | | | |
|---|---|---|---|
| JP | 4-227629 | 8/1992 | |
| JP | 11-180899 | 7/1999 | |
| JP | 2000-344735 | 12/2000 | |
| JP | 2001-151724 | 6/2001 | |
| JP | 2008-542287 | 11/2008 | |
| WO | WO 01/74774 | 10/2001 | |
| WO | WO 03/000657 | 1/2003 | |
| WO | WO 03/000680 | 1/2003 | |
| WO | WO 03/016302 | 2/2003 | |
| WO | WO 2004/058715 | 7/2004 | |
| WO | WO 2005/047296 | 5/2005 | |
| WO | WO 2007/032498 | 3/2007 | |
| WO | WO 2008/129846 | 10/2008 | |
| WO | WO 2008129846 | * 10/2008 | .................... 514/301 |
| WO | WO 2008/156159 | 12/2008 | |

OTHER PUBLICATIONS

Author: Abu T.M. Serajuddin Title: Salt formation to improve drug solubility Science, Technology and Outsourcing Section, Novartis Pharmaceuticals Corporation Advanced Drug Delivery Reviews 59 (2007) 603-616; Elsevier, available online May 29, 2007.*
U.S. Appl. No. 13/231,081, filed Sep. 2, 2011, Koutarou Kawanami.
U.S. Appl. No. 13/228,928, filed Sep. 9, 2011, Takeo Koyama.
Kozma, D., "CRC Handbook of Optical Resolutions Via Diastereomeric Salt Formation", CRC Press: Washington, DC, Chapters 4, 5, and 6 (2002).
Murakami, "Asymmetric Transformation of a Racemic a-(Phthalimidooxy)arylacetic Ester by a Combination of Preferential Crystallization and Simultaneous Racemization" *Chirality* 5 141-48 (1993).
Allan, R., "Synthesis of analogs of GABA. VI. Stereoisomers of cis-3-aminocyclohexanecarboxylic acid" *Australian Journal of Chemistry*, 34(10):2231-36 (Abstract only).
Chiappe, et al. "Nucleophilic Displacement Reactions in Ionic Liquids: Substrate and Solvent Effect in the Reaction of NaN$_3$ and KCN with Alkyl Halides and Tosylates," *Journal of Organic Chemistry* 68:6710-15 (2003).
Betti, C., et al. "Reactivity of anionic nucleophiles in ionic liquids and molecular solvents," *Tetrahedron* 64:1689 (2008).
Blagden, N., et al. "Crystal engineering of active pharmaceutical ingredients to improve solubility and dissolution rates." *Advanced Drug Delivery Reviews*, 59:603-616 (2007).
Serajuddin, A., "Salt formation to improve drug solubility." *Advanced Drug Delivery Reviews*, 59:617-630 (2007).
Ohta, T., et al. "Preparation of N,N'-bis(heterocyclic acyl)cycloalkanediamine and heterocyclediamine derivatives as inhibitors of activated blood coagulation factor X (factor Xa)", Hcaplus 2003:5928 (2003).

(Continued)

*Primary Examiner* — Janet Epps-Smith
*Assistant Examiner* — Yanzhi Zhang
(74) *Attorney, Agent, or Firm* — Locke Lord LLP (57) ABSTRACT

It is desired to provide a pharmaceutical composition containing a compound represented by formula (I) or a pharmacologically acceptable salt thereof, or a solvate thereof, which exhibits an inhibitory effect on activated blood coagulation factor X (FXa), and is useful as an agent for preventing and/or treating thrombosis, wherein the pharmaceutical composition exhibits favorable dissolution properties. The present invention relates to a solid pharmaceutical composition containing a compound represented by formula (I) or a pharmacologically acceptable salt thereof, or a solvate thereof, wherein the content of the compound represented by formula (I) is 0.5% by weight or more and less than 15% by weight with respect to the total weight of the pharmaceutical composition.

9 Claims, 3 Drawing Sheets

OTHER PUBLICATIONS

Dubois, D., et al., "Clinical calorimetry. X. A formula to estimate the approximate surface area if the height and weight be known" *Archives of Internal Medicine*, 17, 863-71 (1916).

Elodi, S., et al., "Optimization of conditions for the catalytic effect of the factor IXa-factor VIII complex: probable role of the complex in the amplification of blood coagulation" *Thrombosis Research*, 15(5-6), 617-29 (1979).

Fujimoto, et al., "Studies on the physical surface area of Japanese: Part 18 calculation formulas in three stages over all age" *Japanese Journal of Hygene*, vol. 23(5): 443-450 (1968)—(Contains an English Abstract).

Furugohri, T., et al., "DU-176b, A potent and orally active factor Xa inhibitor: In vitro and in vivo pharmacological profiles" *Journal of Thrombosis and Haemostasis*, 6(9), 1542-1549 (2008).

Goldberg, SI, et al., "Correlation of configuration and rotatory direction for several 4-substituted cyclohexenes" *Journal of Organic Chemistry*, 31:240-243 (1966).

Hylek, E.M., "Drug evaluation: DU-176b, an oral, direct Factor Xa antagonist." Current Opinion in Investigational Drugs, 8, (9), 778-783 (2007).

Johansson, LC, et al., "Comparison of the Pharmacokinetics and Pharacodynamics of Ximelagatran in young and elderly, healthy Japanese men" *Blood* 100, 3980 (2002).

Mendell, J., et al., "The pharmacokinetics and pharmacodynamics of the direct factor Xa inhibitor, edoxaban co-administered with digoxin: a randomized, open-label, dual treatment sequence, parallel-group study" *Journal of Clinical Pharmacology*, 49(9), 1125 (2009).

Mendell, J., et al., "Thorough QT/QTC study with edoxaban to evaluate effect of therapeutic and supratherapeutic exposure on QTC interval duration in healthy subjects" *Journal of Clinical pharmacology* 49(9), 1122 (2009).

Mould, D., et al., "A population pharmacokinetic pharmacodynamic and logistic regression analysis of lotrafiban in patients" *Clinical Pharmacology and Therapeutics* 69(4), 210-222 (2001).

Mueck, W., et al., "Population pharmacokinetics and pharmacodynamic of rivaroxaban—an oral, direct factor Xa inhibitor—in patients undergoing major orthopaedic surgery" *Clinical Pharmacokinetics*, 47(3), 203-216 (2008).

Nohira, H. "4 Diastereomer Method", Edited by CSJ: The Chemical Society of Japan, kogaku Iseitai no Bunri Kikan Kagaku Sosetsu No. 6, 3rd edition, Japan Scientific Societies Press, pp. 45 to 54, (1999).

Product Information, Clexane ® and Clexane ® Forte, Clexane ® PI MKT, #6178v16, pp. 1-19 (2008).

Ridout, G., et al., "Effect of renal function on edoxaban pharmacokinetics (PK) and on population PK/PK-PD model" *Journal of Clinical Pharmcology* 49(9), 1124 (2009).

Schwartz, HM, et al., "Predicting the Enantiomeric Selectivity of Chymotrypsin. Homologous Series of Ester Substrates" *J. Am. Chem. Soc.*, 100, 5199-5203, (1978).

Sixma JJ, et al., "The ideal anti-thrombotic drug" *Thrombosis research*, 68(6), 507-12 (1992).

Takahashi, H. "3.Warfarin Oto no kojinsa" *Kessen to Junkan*, 14(3), 198-202 (2006) (English Translation Provided).

Tanyeli, C, et al., "Enzyme catalyzed reverse enantiomeric separation of methyl (±)-3-cyclohexene-1-carboxylate" *Tetrahedron: Asymmetry*, 15, 2057-2060, (2004).

Trost, BM, et al., "An Asymmetric Synthesis of (+)-Phyllanthoci" Tetrahedron Lett., 32, 1613-1616, (1991).

Vene, N., et al., "High D-dimer levels predict cardiovascular events in patients with chronic atrial fibrillation during oral anticoagulant therapy" *Thrombosis and Haemostasis*, 90(6), 1163-1172 (2003).

International Preliminary Report on Patentability, issued in PCT/JP2009/070613, mailed Jul. 5, 2011.

International Search Report, issued in PCT/JP2009/070613, mailed Feb. 16, 2010.

Written Opinion of the International Searching Authority, issued in PCT/JP2009/070613, mailed Jul. 5, 2011.

International Preliminary Report on Patentability, issued in PCT/JP2009/070874, mailed Jul. 5, 2011.

International Search Report, issued in PCT/JP2009/070874, mailed Mar. 23, 2010.

Written Opinion of the International Searching Authority, issued in PCT/JP2009/070874, mailed Jul. 5, 2011.

International Preliminary Report on Patentability, issued in PCT/JP2009/071016, mailed Jul. 5, 2011.

International Search Report, issued in PCT/JP2009/071016, mailed Feb. 16, 2010.

Written Opinion of the International Searching Authority, issued in PCT/JP2009/071016, mailed Jul. 5, 2011.

International Preliminary Report on Patentability, issued in PCT/JP2010/050128, mailed Aug. 16, 2011.

International Search Report, issued in PCT/JP2010/050128, mailed Apr. 6, 2010.

Written Opinion of the International Searching Authority, issued in PCT/JP2010/050128, mailed Aug. 16, 2011.

International Preliminary Report on Patentability, issued in PCT/JP2010/057990, mailed Dec. 12, 2011.

International Search Report, issued in PCT/JP2010/057990, mailed Jun. 8, 2010.

Written Opinion of the International Searching Authority, issued in PCT/JP2010/057990, mailed Dec. 12, 2011.

International Preliminary Report on Patentability, issued in PCT/JP2010/060261, mailed Dec. 20, 2011.

International Search Report, issued in PCT/JP2010/060261, mailed Sep. 21, 2010.

Written Opinion of the International Searching Authority, issued in PCT/JP2010/060261, mailed Dec. 20, 2011.

PCT International Preliminary Report on Patentability of Int'l App. No. PCT/JP2010/053905 dated Oct. 18, 2011, 5 pages.

International Search Report of Int'l App. No. PCT/JP2010/053905 dated Apr. 21, 2010, 2 pages.

English Translation of PCT Written Opinion of the International Searching Authority of Int'l App. No. PCT/JP2010/053905 dated May 11, 2010, 4 pages.

PCT International Preliminary Report on Patentability of Int'l App. No. PCT/JP2010/053976 dated Oct. 18, 2011, 5 pages.

International Search Report of Int'l App. No. PCT/JP2010/053976 dated Apr. 13, 2010, 2 pages.

English Translation of PCT Written Opinion of the International Searching Authority of Int'l App. No. PCT/JP2010/053976 dated Apr. 13, 2010, 4 pages.

Patani, et al., "Bioisosterism: A rational approach in drug design", *Chem. Rev.* 1996, 3147-3176.

U.S. Appl. No. 13/157,590, filed Jun. 10, 2011, Koji Sato.
U.S. Appl. No. 13/162,922, filed Jun. 17, 2011, Takeo Koyama.
U.S. Appl. No. 13/163,287, filed Jun. 17, 2011, Takashi Abiko.
U.S. Appl. No. 13/181,596, filed Jul. 13, 2011, Makoto Ono.
U.S. Appl. No. 13/273,360, filed Oct. 14, 2011, Toshiharu Yoshino.
U.S. Appl. No. 13/554,610, filed Jul. 20, 2012, Tetsuya Kimura.
U.S. Appl. No. 13/622,783, filed Sep. 19, 2012, Tetsuya Suzuki.

Supplementary European Search Report mailed Jun. 4, 2012 in EP Application No. 09 83 3467, which corresponds to U.S. Appl. No. 13/163,287.

Furugohri, T, et al, "Pharmaceutical Characterization, Antithromboti and Bleeding Effects of DU-176b", Journal of Thrombosis and Haemostasis, 3(supp. 1), Abstract P1110, (2005).

Zafar, UM, et al., "Antithrombotic effects of factor Xa inhibition with DU-176b: Phase-I study of an oral, direct factor Xa inhibitor using an ex-vivo flow chamber", Thrombosis and Haemostasis, 98(4):833-888 (2007).

Walker, MB, "Understanding the PT-INR Test", obtained from the internet www.vclotacare.com/ptinr.aspx (retrieved Apr. 24, 2012).

Anonymous, "A phase 2, randomized, parallel group, multi-center, multi-national study for the evaluation of safety and efficacy of two fixed dosages of DU-176b in subjects with non-valvular atrial fibrillation", Clinical Trials.gov NCT00806624 obtained from the internet clinicaltrials.gov/archive/NCT00806624/2008_12_10 (retrieved Apr. 23, 2012).

Thomas, M., et al, "Management of Venous Thromboembolism", *Arch Intern Med.*, 163:759-768 (2003).

Turpie, Agg., "Oral, direct factor Xa inhibitors in development for the prevention and treatment of thromboembolic diseases", *Arteriosclerosis, Thrombosis, and Vascular Biology*, 27:1238-1247 (2007).

De Caterina, R, et al. "Anticoagulants in heart disease: current status and perspectives", *European Heart Journal* 28:880-913 (2007).

Dyke, CK., "First experience with direct factor Xa inhibition in patients with stable coronary disease: a pharmacokinetic and pharmacodynamics evaluation", *Circulation.*, 105:2385-2391 (2002).

Iba, T., et al., "Factor Xa-inhibitor (DX-9065a) modulates the leukocyte-endothelial cell interaction in endotoxemic rat", *Shock.*, 17(2):159-162 (2002).

Office of Generic Drugs, "Scoring Configuration of Generic Drug Products", dated Nov. 1, 1995; www.fda.gov/downloads/AboutFDA/CentersOffices/CDER/ManualofPoliciesProcedures/ucm079779.pdf; accessed Sep. 6, 2012; cited in U.S. Appl. No. 13/163,287.

International Search Report, issued in related International Application No. PCT/JP2011/055955, mailed May 24, 2011.

Written Opinion of the International Searching Authority, issued in related International Application No. PCT/JP2011/055955, mailed May 24, 2011.

\* cited by examiner

PHARMACEUTICAL COMPOSITION HAVING IMPROVED SOLUBILITY

This application is a continuation of International Application No. PCT/JP2010/060261, filed on Jun. 17, 2010, entitled "PHARMACEUTICAL COMPOSITION HAVING IMPROVED SOLUBILITY", which claims the benefit of Japanese Patent Application Number JP 2009-145112, filed on Jun. 18, 2009, all of which are hereby incorporated by reference.

FIELD OF THE INVENTION

The present invention relates to a solid pharmaceutical composition that is improved in its dissolution properties, containing a compound that exhibits an inhibitory effect on activated blood coagulation factor X, and that is useful as a preventative and/or therapeutic drug for thrombotic diseases.

BACKGROUND OF THE INVENTION $N^1$-(5-chloropyridin-2-yl)-$N^2$-(4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (I):

[Formula 1]

(I)

or a pharmacologically acceptable salt thereof, or a solvate thereof (in the present specification, the compound represented by formula (I) is referred to as compound I, and compound I, a pharmacologically acceptable salt thereof, and solvates thereof are also collectively referred to as compound I, etc.) is known to exhibit a potent inhibitory effect on activated blood coagulation factor X (activated factor X; hereinafter, also referred to as FXa in the present specification) and be useful as a pharmaceutical drug, particularly, an activated blood coagulation factor X inhibitor (hereinafter, also referred to as an FXa inhibitor or anti-FXa in the present specification) and/or an agent for preventing and/or treating thrombosis or embolism (Patent Documents 1 to 4).

Compound I is a basic compound that exhibits favorable solubility in a strongly acidic aqueous solution, but reduced solubility in a neutral aqueous solution (e.g., a neutral buffer). A pharmaceutical composition containing compound I, etc. as an active ingredient also exhibits poor dissolution properties of compound I, etc. in a neutral aqueous solution. A method comprising coating a composition containing compound I, etc. with one or two or more coating agents selected from a cellulose derivative, a polyvinyl compound, an acrylic acid derivative, and a saccharide is known as a method for improving the dissolution properties of compound I, etc. in the neutral region of a solid pharmaceutical composition containing compound I, etc. as an active ingredient (Patent Document 4). Patent Document 4 discloses a pharmaceutical composition wherein the content of compound I is 15% by weight with respect to the total weight of the pharmaceutical composition.

Citation List
Patent Document
Patent Document 1: WO 2003/000657
Patent Document 2: WO 2003/000680
Patent Document 3: WO 2003/016302
Patent Document 4: WO 2008/129846

SUMMARY OF INVENTION

Technical Problem

An object of the present invention is to find a novel method for improving the dissolution properties in the neutral region of a pharmaceutical composition containing compound I, etc. and thereby provide a solid pharmaceutical composition containing compound I, etc. as an active ingredient and having favorable dissolution properties in the neutral region.

Solution to Problem

As a result of conducting diligent studies, the present inventors have found that, surprisingly, the dissolution rate of compound I, etc. from a pharmaceutical composition can be improved drastically by a very simple method of adjusting the proportion of compound I, etc. in the pharmaceutical composition. Based on this finding, the present invention has been completed.

Specifically, the present invention relates to:

[1] a solid pharmaceutical composition containing $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide represented by the following formula (I):

[Formula 2]

(I)

or a pharmacologically acceptable salt thereof, or a solvate thereof, wherein the content of the compound represented by formula (I) is 0.5% by weight or more and less than 15% by weight with respect to the total weight of the pharmaceutical composition;

[2] the pharmaceutical composition according to [1], wherein the pharmaceutical composition contains the compound represented by formula (I) at 5% by weight or more and 10% by weight or less with respect to the total weight of the pharmaceutical composition;

[3] the pharmaceutical composition according to [1] or [2], wherein the dosage form is a tablet;

[4] the pharmaceutical composition according to any one of [1] to [3], wherein the tablet has a density of 1.2 mg/mm³ to 1.4 mg/mm³;

[5] the pharmaceutical composition according to any one of [1] to [4], wherein the pharmaceutical composition further contains a sugar alcohol and a water-swelling additive as excipients;
[6] the pharmaceutical composition according to [5], wherein the sugar alcohol is D-mannitol or erythritol, and the water-swelling additive is pregelatinized starch or crystalline cellulose;
[7] the pharmaceutical composition according to [6], wherein the sugar alcohol is D-mannitol, and the water-swelling additive is pregelatinized starch;
[8] the pharmaceutical composition according to [7], wherein, when the composition is subjected to a dissolution test by the paddle method at a rotation rate of 50 rpm, the composition exhibits an average percentage dissolution of the compound represented by formula (I), in a dissolution test medium having a pH of 6.8, of 60% or higher in 30 minutes after the start of the dissolution test and 80% or higher in 60 minutes after the start;
[9] the pharmaceutical composition according to [8], wherein, when the composition is subjected to a dissolution test by the paddle method at a rotation rate of 50 rpm, the composition exhibits an average percentage dissolution of the compound represented by formula (I), in a dissolution test medium having a pH of 6.8, of 70% or higher in 30 minutes after the start of the dissolution test and 80% or higher in 60 minutes after the start;
[10] the pharmaceutical composition according to any one of [1] to [9], which is coated with one or more coating agents selected from a cellulose derivative, a polyvinyl compound, an acrylate derivative, or a saccharide;
[11] the pharmaceutical composition according to any one of [1] to [10], wherein the coating agents are one or more species selected from the group comprising hypromellose, methylcellulose, ethylcellulose, hydroxypropyl cellulose, polyvinyl alcohol, povidone, vinyl acetate resin, polyvinyl acetal diethylaminoacetate, aminoalkyl methacrylate copolymer RS, ethyl acrylate-methyl methacrylate copolymer dispersion, sucrose, and mannitol;
[12] the pharmaceutical composition according to any one of [1] to [11], wherein the compound represented by formula (I) or a pharmacologically acceptable salt thereof, or a solvate thereof is $N^1$-(5-chloropyridin-2-yl)-$N^2$-((1S,2R, 4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate represented by the following formula (Ia):

Advantageous Effects of the Invention

The present invention provides a pharmaceutical composition containing compound I, etc. and having favorable dissolution properties in the neutral range.

DETAILED DESCRIPTION

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (compound I) represented by the following formula (I):

[Formula 4]

(I)

[Formula 3]

(Ia)

is called edoxaban (N-(5-chloropyridin-2-yl)-N'-[(1S,2R, 4S)-4-(N,N-dimethylcarbamoyl)-2-(5-methyl-4,5,6,7-tetrahydro[1,3]thiazolo[5,4-c]pyridine-2-carboxamido)cyclohexyl]oxamide) as International Nonproprietary Name (INN).

Compound I may be a solvate (including hydrates) or may be a pharmacologically acceptable salt or a solvate (including hydrates) of the salt.

Examples of the salt of compound I include hydrochloride, sulfate, hydrobromide, citrate, hydroiodide, phosphate, nitrate, benzoate, methanesulfonate, benzenesulfonate, 2-hydroxyethanesulfonate, p-toluenesulfonate, acetate, propionate, oxalate, malonate, succinate, glutarate, adipate, tartrate, maleate, fumarate, malate, and mandelate.

The salt of compound I is preferably hydrochloride, methanesulfonate, or p-toluenesulfonate, particularly preferably p-toluenesulfonate.

Preferable examples of compound I or a pharmacologically acceptable salt thereof, or a solvate thereof can include the following compounds: $N^1$-(5-chloropyridin-2-yl)-$N^2$-((1S, 2R, 4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide; $N^1$-(5-chloropyridin-2-yl)-$N^2$-((1S, 2R, 4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride; $N^1$-(5-chloropyridin-2-yl)-$N^2$-((1S, 2R, 4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate; and $N^1$-(5-chloropyridin-2-yl)-$N^2$-((1S, 2R, 4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate (hereinafter, also referred to as compound Ia) represented by the following formula (Ia):

[Formula 5]

(Ia)

The compound I or a pharmacologically acceptable salt thereof, or a solvate thereof can be produced by a method described in Patent Documents 1 to 4 or a method equivalent thereto.

The efficacy and safety of pharmaceutical compositions for oral administration such as tablets are largely influenced by the dissolution properties of the active ingredient(s). Thus, the criteria regarding the dissolution properties are defined in each country. For example, in Japan, the USA, and Europe, the pharmacopoeia specifies a method for a dissolution test. In the dissolution test, various dissolution media (hereinafter, also referred to as test solutions or eluting solutions) are used. These dissolution media are adjusted to a pH range of 1 to 8. For example, strongly acidic dissolution media (e.g., JP 1st fluid described in the Japanese Pharmacopoeia and 0.1 N hydrochloric acid solutions), dissolution media of pH 3 to 5 (e.g., acetic acid-sodium acetate buffers and McIlvaine buffer), dissolution media of pH 6.8 (e.g., JP 2nd fluid described in the Japanese Pharmacopoeia and phosphate buffers of pH 6.8), and water are shown as the dissolution media specified by the pharmacopoeia or the like of each country. Preparations for oral administration are required to have favorable dissolution properties in dissolution tests using these dissolution media.

Compound I is a basic compound that exhibits favorable solubility in a strongly acidic aqueous solution, but reduced solubility in a neutral aqueous solution (neutral buffer, etc.). A pharmaceutical composition containing compound I, etc. also exhibits poor dissolution properties of compound I, etc. in an aqueous solution with neutral pH. One of the features of the present invention is to enhance the dissolution rate of compound I, etc. from a pharmaceutical composition for oral administration containing compound I, etc. in the neutral range by adjusting the proportion of compound I, etc. in the pharmaceutical composition. Specifically, the present invention provides a solid pharmaceutical composition for oral administration wherein compound I, etc. is contained at a proportion in a certain range in the pharmaceutical composition. Specifically, in a dissolution test conducted at 50 rpm by the paddle method in a dissolution medium of pH 6.8, the solid pharmaceutical composition (e.g., tablet) of the present invention containing compound I, etc. at 0.5% by weight or more and less than 15% by weight, calculated in terms of compound I, exhibited dissolution properties more favorable than the average percentage dissolution of a solid pharmaceutical composition (e.g., tablet) containing compound I, etc. at 15% by weight or more, calculated in terms of compound I. Moreover, the pharmaceutical composition of the present invention was improved in terms of the variation in the dissolution of compound I, etc. among preparations (e.g., tablets).

The amount of compound I contained in the pharmaceutical composition is preferably less than 15% by weight, more preferably 14% by weight or less, 13% by weight or less, 12.5% by weight or less, 12% by weight or less, 11% by weight or less, or 10% by weight or less as the upper limit and is preferably 0.5% by weight or more, more preferably 1% by weight or more, 2% by weight or more, 2.5% by weight or more, 3% by weight or more, 4% by weight or more, or 5% by weight or more as the lower limit, with respect to the total weight of the pharmaceutical composition. The upper and lower limits are preferably 0.5% by weight or more and less than 15% by weight, more preferably 2.5% by weight or more and 12.5% by weight or less, even more preferably 5% by weight or more and 10% by weight or less, with respect to the total weight of the pharmaceutical composition. In the present specification, the "amount of compound I contained in the pharmaceutical composition" refers to the weight of a free form of the compound represented by formula (I). For the pharmaceutical composition containing the pharmacologically acceptable salt of a free form of the compound represented by formula (I) or the solvate thereof as an active ingredient, the weight of the pharmacologically acceptable salt or the solvate thereof is converted to that of the free form, and the pharmaceutical composition forms a part of the present invention when the proportion of this converted weight to the whole pharmaceutical composition falls within the range described above. For example, 40.4 mg of compound Ia is converted to 30 mg as the weight of the free form. Thus, 300 mg (total weight) of the pharmaceutical composition containing 40.4 mg of compound Ia as an active ingredient is calculated as containing 10% by weight of compound I and is included in the scope of the present invention.

The amount of compound I, etc. contained in one unit of the pharmaceutical composition (e.g., tablet or capsule) is usually 1 to 100 mg, preferably 5 to 100 mg, more preferably 5 to 75 mg, even more preferably 15 to 60 mg, in terms of the free form of compound I.

The present invention also relates to a solid pharmaceutical composition for oral administration containing compound I, etc. at the proportion described above, wherein the pharmaceutical composition is coated with coating agents.

The solid pharmaceutical composition for oral administration of the present invention containing compound I, etc. and coating agents is not limited to coated solid preparations such as coated tablets and encompasses various solid preparations comprising coating agents. For example, a solid preparation containing compound I, etc., wherein coating agents are formulated in a matrix form in the solid preparation is also included in the present invention.

Examples of the coating agents can include coating agents generally employed in pharmaceutical manufacturing for coating tablets and granules therewith. Preferably, the coating agent has low solubility within the pH range in the intestine. Specifically, a coating agent which is difficult to dissolve within the pH range in the intestine is generally preferred, as compared with an enteric coating agent.

Specific examples of the preferred coating agents include the following:
(1) cellulose derivatives such as hypromellose (hydroxypropyl methylcellulose), hydroxypropyl cellulose, ethyl cellulose, and methyl cellulose;
(2) polyvinyl compounds such as polyvinyl alcohol, povidone (polyvinylpyrrolidone), polyvinyl acetal diethylaminoacetate, and a polyvinyl acetate resin;
(3) acrylate derivatives such as an aminoalkyl methacrylate copolymer RS and an ethyl acrylate-methyl methacrylate copolymer dispersion; and
(4) saccharides (including sugar alcohols) such as sucrose and mannitol, which are used as sugar coating agents. These coating agents may be used singly or in combination of two or more species. Hypromellose or a hypromellose-based coating agent includes species such as hypromellose 2208, hypromellose 2906, and hypromellose 2910 having different viscosities (mPa S). These species having different viscosities may be used singly or in combination of two or more species.

Among these, preferred are one or more species selected from the group consisting of cellulose derivatives (hypromellose, methyl cellulose, ethyl cellulose, methyl cellulose, or hydroxypropyl cellulose); polyvinyl compounds (polyvinyl alcohol, povidone, polyvinyl acetate resin, or polyvinyl acetal, diethylaminoacetate); acrylate derivatives (amino alkyl methacrylate copolymer RS and ethyl acrylate-methyl methacrylate copolymer dispersion); and saccharides (including sugar alcohols) (sucrose and mannitol).

Of these, one or more species selected from among cellulose derivatives and polyvinyl compounds are more preferred. Still more preferred are one or more species selected from among hypromellose, ethyl cellulose, and polyvinyl alcohol. Among them, hypromellose is particularly preferred.

In the present invention, the aforementioned coating agent and other additives required for preparing a coating suspension (e.g., a plasticizer) may be incorporated in combination into the composition. Examples of the additives required for preparing a coating suspension (e.g., plasticizer) include Macrogols (polyethylene glycols having an average molecular weight of 1,000 to 35,000) such as Macrogol 1000, Macrogol 1500, Macrogol 1540, Macrogol 4000, Macrogol 6000, Macrogol 8000, Macrogol 20000, and Macrogol 35000; glycerin fatty acid ester; sucrose fatty acid ester; castor oil; triethyl citrate; triacetin; or talc. The aforementioned coating agents may further contain the below-mentioned coloring agent, and the mixture may be incorporated into the pharmaceutical composition of the present invention.

The pharmaceutical composition of the present invention contains 0.5 to 20% by weight, preferably 1.0 to 15% by weight, more preferably 1.5 to 10% by weight of the coating agents.

In the present invention, the solid preparation containing compound I etc. may be coated with the aforementioned coating agent through a widely known coating process for solid preparation coating. No particular limitation is imposed on the coating process, and for example, there may be employed a spray coating process in which a solution/dispersion of the coating agent is sprayed onto a solid preparation containing compound I etc. by means of a fluidized bed coater or a pan coater, a dip coating process in which a solid preparation containing compound I etc. is dipped in a coating suspension; and a dry coating process employing impact in a gas flow. The solid preparation containing compound I etc. which has not been subjected to the coating process may be produced through a conventionally known process.

Thus, the pharmaceutical composition of the present invention may be produced by preparing a solid preparation containing compound I, etc. as a pharmaceutically active ingredient through a known method and then coating the thus prepared solid preparation with a coating agent.

No particular limitation is imposed on the solid preparation containing compound I, etc. which has not been subjected to the coating process. However, preferred embodiments will next be described.

Excipients used in the production of the solid preparation such as a tablet are not particularly limited, and excipients usually used by those skilled in the art can be used.

Preferable examples of the excipients include a sugar alcohol, a water-swelling additive, and their combination.

The sugar alcohol is preferably mannitol, erythritol, or xylitol, or the like, particularly preferably mannitol.

The water-swelling additive employed in the present invention means an additive for pharmaceuticals which swells with water added thereto. Examples of the water-swelling additive in the present invention include excipients and bases having water swellability. Specific examples of the water-swelling additive include pregelatinized starch, gelatinized starch, crystalline cellulose, sodium carboxymethyl starch, carmellose (carboxymethyl cellulose), carmellose calcium, croscarmellose sodium (croscarboxymethyl cellulose sodium), soybean lecithin, low-substituted hydroxypropyl cellulose, tragacanth powder, and bentonite. These water-swelling additives may be employed singly or in combination of two or more species.

Among these water-swelling additives, pregelatinized starch and crystalline cellulose are preferred, with pregelatinized starch being more preferable. As crystalline cellulose, Ceolus (manufactured by Asahi Kasei Corp.) is particularly preferred. As The pregelatinized starch, PCS (manufactured by Asahi Kasei Corp.) or Starch 1500 (manufactured by Colorcon Japan Ltd.) are particularly preferred.

To the composition of the present invention, a water-soluble excipient other than sugar alcohols may be added. Examples of the water-soluble excipient include: fructose, purified sucrose, sucrose, purified sucrose spherical granules, lactose, anhydrous lactose, sucrose-starch spherical granules, semi-digested starch, glucose, glucose hydrate, powder sugar, pullulan, and β-cyclodextrin. Other than saccharides, examples further include aminoethylsulfonic acid, maltose syrup powder, sodium chloride, citric acid, sodium citrate, glycine, calcium gluconate, L-glutamine, tartaric acid, potassium hydrogentartrate, ammonium carbonate, dextran 40, dextrin, calcium lactate, povidone, Macrogol (polyethylene glycol) 1500, Macrogol 1540, Macrogol 4000, Macrogol 6000, anhydrous citric acid, DL-malic acid, sodium hydrogen phosphate, potassium dihydrogenphosphate, and sodium dihydrogenphosphate.

The water-soluble excipient is preferably selected from saccharides. Specific examples include purified sucrose, sucrose, lactose, lactose granules, glucose, glucose hydrate, powder sugar, or pullulan. Of these, lactose is even more preferred.

The solid preparation containing compound I, etc. preferably contains a sugar alcohol in an amount of 0.01 to 99.0 wt. %, preferably 20 to 80 wt. %, more preferably 40 to 60 wt. %. Also, the solid preparation containing compound I preferably contains a water-swelling additive in an amount of 0.01 to 90 wt. %, preferably 0.1 to 80 wt. %, more preferably 5 to 50 wt. %.

In the case where the solid preparation contains the aforementioned water-swelling additive and sugar alcohol, the ratio of water-swelling additive to sugar alcohol in the preparation is preferably 0.05 to 50 parts by weight (sugar alcohol) to 1 part by weight (water-swelling additive), more preferably 1 to 10 parts by weight (sugar alcohol), particularly preferably 1.5 to 4 parts by weight (sugar alcohol).

In addition to the combination of aforementioned sugar alcohol and water-swelling additive, the pharmaceutical composition containing compound I etc. may further contain a water-insoluble excipient, a disintegrant, a binder, a fluidizing agent, a lubricant, a coloring agent, a polishing agent, etc., so long as the effects of the present invention are not impaired.

Examples of the water-insoluble excipient include L-aspartic acid, alginic acid, carmellose sodium, hydrous silicon dioxide, crospovidone, calcium glycerophosphate, magnesium silicate aluminate, calcium silicate, magnesium silicate, light anhydrous silicic acid, crystalline cellulose, cellulose powder, synthetic aluminum silicate, synthetic aluminum silicate/hydroxypropyl starch/crystalline cellulose, flour, wheat starch, wheat germ flour, wheat germ oil, rice powder, rice starch, cellulose acetate phthalate, titanium oxide, magnesium oxide, dihydroxyaluminum aminoacetate, calcium tertiary phosphate, talc, calcium carbonate, magnesium carbonate, precipitated calcium carbonate, natural aluminum silicate, corn starch, granulated corn starch, potato starch, hydroxypropyl cellulose, hydroxypropyl starch, calcium hydrogenphosphate anhydrous, granulated calcium hydrogenphosphate anhydrous, or calcium dihydrogenphosphate. Of these, crystalline cellulose or cellulose powder are preferred as a water-insoluble excipient.

Examples of the disintegrant include adipic acid, alginic acid, gelatinized starch, sodium carboxymethyl starch, carmellose, carmellose calcium, carmellose sodium, hydrous silicon dioxide, calcium citrate, croscarmellose sodium, crospovidone, light anhydrous silicic acid, crystalline cellulose, synthetic aluminum silicate, wheat starch, rice starch, cellulose acetate phthalate, calcium stearate, low-substituted hydroxypropyl cellulose, corn starch, tragacanth powder, potato starch, hydroxyethylmethyl cellulose, hydroxypropyl starch, pregelatinized starch, monosodium fumarate, povidone, anhydrous citric acid, methyl cellulose, or calcium dihydrogenphosphate. Of these, crospovidone or sodium carboxymethyl starch are preferred as a disintegrant.

Examples of the binder include maltose syrup powder, gum arabic, gum arabic powder, sodium alginate, propylene glycol alginate ester, hydrolyzed gelatin powder, hydrolyzed starch-light anhydrous silicic acid, fructose, carboxyvinyl polymer, carboxymethylethyl cellulose, hydrous silicon dioxide, agar powder, light anhydrous silicic acid, light anhydrous silicic acid-containing hydroxypropyl cellulose, crystalline cellulose, synthetic aluminum silicate, high-molecular polyvinylpyrrolidone, copolydone, wheat flour, wheat starch, rice flour, rice starch, polyvinyl acetate resin, cellulose acetate phthalate, dioctyl sodium sulfosuccinate, dihydroxyaluminum aminoacetate, sodium potassium tartrate, water, sucrose fatty acid ester, purified gelatin, purified sucrose, gelatin, D-sorbitol, dextrin, starch, corn starch, tragacanth, tragacanth powder, lactose, concentrated glycerin, sucrose, potato starch, hydroxyethylcellulose, hydroxyethylmethyl cellulose, hydroxypropyl cellulose, hydroxypropyl starch, hydroxypropylmethyl cellulose 2208, hydroxypropylmethyl cellulose 2906, hydroxypropylmethyl cellulose 2910, hydroxypropylmethyl cellulose phthalate, vinylpyrrolidone-vinyl acetate copolymers, piperonyl butoxide, glucose, pregelatinized starch, fumaric acid, fumaric acid-stearic acid-polyvinyl acetal diethylaminoacetate-hydroxypropylmethyl cellulose 2910 mixtures, pullulan, povidone, polyvinyl alcohol (completely saponified product), polyvinyl alcohol (partially saponified product), sodium polyphosphate, macrogol 4000, macrogol 6000, macrogol 20000, D-mannitol, or methylcellulose.

Examples of the fluidizing agent include hydrous silicon dioxide, light anhydrous silicic acid, crystalline cellulose, synthetic aluminum silicate, titanium oxide, stearic acid, calcium stearate, magnesium stearate, calcium tertiary phosphate, talc, corn starch, or magnesium aluminometasilicate.

Examples of the lubricant include cocoa fat, carnauba wax, hydrous silicon dioxide, dry aluminum hydroxide gel, glycerin fatty acid ester, magnesium silicate, light anhydrous silicic acid, crystalline cellulose, hardened oil, synthetic aluminum silicate, white beeswax, magnesium oxide, sodium potassium tartrate, sucrose fatty acid ester, stearic acid, calcium stearate, magnesium stearate, stearyl alcohol, polyoxyl 40 stearate, cetanol, soybean hardened oil, gelatin, talc, magnesium carbonate, precipitated calcium carbonate, corn starch, potato starch, fumaric acid, stearyl sodium fumarate, Macrogol 600, Macrogol 4000, Macrogol 6000, beeswax, magnesium metasilicate aluminate, sodium laurate, or magnesium sulfate.

Examples of the coloring agent can include yellow iron sesquioxide, iron sesquioxide, titanium oxide, orange essence, brown iron oxide, β-carotene, black iron oxide, food blue No. 1, food blue No. 2, food red No. 2, food red No. 3, food red No. 102, food yellow No. 4, and food yellow No. 5.

Examples of the polishing agent include carnauba wax, hardened oil, a polyvinyl acetate resin, white beeswax, titanium dioxide, stearic acid, calcium stearate, polyoxyl 40 stearate, magnesium stearate, purified shellac, purified paraffin/carnauba wax mixture, cetanol, talc, colored silver foil, white shellac, paraffin, povidone, Macrogol 1500, Macrogol 4000, Macrogol 6000, beeswax, glycerin monostearate, or rosin. Of these, carnauba wax, titanium dioxide, or talc are preferred as a polishing agent.

No particular limitation is imposed on the dosage form of the pharmaceutical composition of the present invention, so long as the solid preparation thereof can be orally administered to a subject. However, the dosage form is preferably a solid preparation, specifically in the form of tablet, granules, powder (including fine granules), or a capsule. The solid preparation may be produced through a widely known production method. In one exemplified procedure, the pharmaceutical composition of the present invention is prepared through mixing the aforementioned compound I, etc., a sugar alcohol, and/or a water-swelling additive, and optional additives such as a disintegrant, a binder, a fluidizing agent, a lubricant, a coloring agent, and a polishing agent, and the mixture is processed through, for example, the method of producing solid preparations described in the general rules for preparations in the Japanese Pharmacopeia.

When the pharmaceutical composition of the present invention is in the dosage form of granules, the granules may be produced through blending compound I etc. with a sugar alcohol and/or a water-swelling additive and optional additives such as an excipient, a binder, a disintegrant, and other appropriate members, and granulating the thus-obtained uniform mixture through an appropriate technique. Additionally, the thus-produced granules may be coated with a coating agent by means of a fluidized bed coater through spraying a suspension/solution of the coating agent onto the granules.

Alternatively, when the pharmaceutical composition of the present invention is in the dosage form of a powder, the powder or microgranules may be produced through blending compound I etc. with a sugar alcohol and/or a water-swelling additive and optional additives such as an excipient, a binder, a disintegrant, and other appropriate members, to form a uniform admixture, and pulverizing or micro-granulating the thus-obtained admixture through an appropriate technique. Additionally, the thus-produced powder or microgranules may be coated with a coating agent by means of a fluidized bed coater through spraying a suspension/solution of the coating agent onto the powder or microgranules.

Alternatively, when the pharmaceutical composition of the present invention is in the dosage form of a capsule, the aforementioned granules or powders may be encapsulated with coating capsules.

Alternatively, when the pharmaceutical composition of the present invention is in the dosage form of a tablet, tablets may be produced directly through compression molding of a powder mixture containing the aforementioned compound I, etc. and acceptable additives for pharmaceuticals, preferably a powder mixture containing aforementioned compound I, etc., a sugar alcohol and/or a water-swelling additive, and acceptable additives for pharmaceuticals. Alternatively, the tablets may be produced through granulating a powder mixture containing the aforementioned compound I, etc. and acceptable additives for pharmaceuticals, preferably, a powder mixture containing the aforementioned compound I, etc., a sugar alcohol and/or a water-swelling additive, and acceptable additives for pharmaceuticals, through a technique such as fluidized-bed granulation or agitation granulation, followed by compression molding of the formed granules. The pressure of compression molding may be determined within an appropriate range, so long as the effect of the present invention is not impaired. The compression molding is preferably performed at, for example, 5 to 20 kN, preferably 6 to 15 kN. When the pharmaceutical composition of the present invention is in the dosage form of a tablet, tablet density is not particularly limited, for example, 1.1 to 1.5 mg/mm$^3$, preferably 1.2 to 1.4 mg/mm$^3$. Moreover, the shape of the tablet is not particularly limited, preferably a lens, disc, round, oval (e.g., caplets), or a polygonal (e.g., triangle or rhombus) shape. Furthermore, the produced tablet may be further coated with a coating agent by means of a pan coater through spraying a suspension/solution of the coating agents onto the tablets.

The dissolution properties of compound I, etc. of the pharmaceutical composition of the present invention can be evaluated by, for example, dissolution tests disclosed in the Japanese Pharmacopoeia, the United States Pharmacopoieia (USP), and the European Pharmacopoeia. Examples of the test medium employed in the dissolution tests will be described.

Non-limiting examples of the aforementioned strongly acidic dissolution medium include the JP 1st fluid described in the Japanese Pharmacopoeia; and "USP 0.1N HCl, Simulated Gastric Fluid without Enzyme" described in the United States Pharmacopoeia.

Non-limiting examples of the dissolution test medium (pH 6.8) include the JP 2nd fluid and phosphate buffer (pH 6.8) described in the Japanese Pharmacopoeia, "USP Phosphate Buffer (pH 6.8)", Simulated Intestinal Fluid without Enzyme described in the United States Pharmacopoeia, and Phosphate Buffer Solution (pH 6.8) described in the European Pharmacopoeia.

Moreover, dissolution test media (pH 3 to 5) may be a test medium having a pH 4.0 or pH 4.5. Specific examples include acetic acid-sodium acetate buffer described in the Japanese Pharmacopoeia, "USP Acetate Buffer" described in the United States Pharmacopoeia, and Acetate Buffer Solution (pH 4.5) described in the European Pharmacopoeia. Moreover, a diluted McIlvaine buffer of pH 4.0 may also be used. However, the dissolution test medium of pH 3 to 5 is not limited to the above examples.

These dissolution test media are prepared through methods described in the corresponding pharmacopoeia or the like of each country. When the employed dissolution test medium is a buffer solution, variation of the pH of the test medium is preferably within ±0.05 of pH defined for each dissolution medium.

When the pharmaceutical composition of the present invention is subjected to the method described in the dissolution test method of the Japanese Pharmacopoeia (paddle method; at a rotation speed of 50 rpm), the composition exhibits an average percentage dissolution of the compound I, in a dissolution test medium having a pH of 6.8, preferably of 70% or higher in 60 minutes after the start of the dissolution test and more preferably of 80% or higher in 60 minutes after the start, even more preferably of 60% or higher in 30 minutes after the start and 80% or higher in 60 minutes after the start, further preferably of 70% or higher in 30 minutes after the start and 80% or higher in 60 minutes after the start.

Moreover, when the composition is subjected to the method described in the dissolution test method of the Japanese Pharmacopoeia (paddle method; at a rotation speed of 50 rpm), the composition exhibits an average percentage dissolution of the compound I, in a dissolution test medium having a pH of 4.5, of 85% or higher in 30 minutes after the start of the dissolution test.

As used herein, the "average percentage dissolution" refers to the average of percentage dissolution values obtained from at least 3, preferably 6, more preferably 12 solid preparation samples for each type of solid preparation.

The pharmaceutical composition of the present invention exhibits a high inhibitory effect on activated blood coagulation factor X (FXa) and as such, is useful as an anticoagulant agent or an agent for preventing and/or treating thrombosis or embolism. The pharmaceutical composition of the present invention is useful as a pharmaceutical drug for mammals including humans, an activated blood coagulation factor X inhibitor, an anticoagulant agent, an agent for preventing and/or treating thrombosis and/or embolism, an agent for preventing and/or treating thrombotic diseases, and further, an agent for preventing (in the present specification, the prevention includes secondary prevention; the same holds true for the description below) and/or treating cerebral infarction, cerebral embolism, pulmonary infarction, pulmonary embolism, myocardial infarction, angina pectoris, thrombus and/or embolism accompanying nonvalvular atrial fibrillation (NVAF), deep vein thrombosis, deep vein thrombosis after surgery, thrombosis after prosthetic valve/joint replacement, thromboembolism after total hip replacement (THR), thromboembolism after total knee replacement (TKR), thromboembolism after hip fracture surgery (HFS), thrombosis and/or reocclusion after revascularization, Buerger's disease, disseminated intravascular coagulation syndrome, systemic inflammatory response syndrome (SIRS), multiple organ dysfunction syndrome (MODS), thrombosis at the time of extracorporeal circulation, or blood coagulation at the time of blood collection.

EXAMPLES

Next, the present invention will be described in detail with reference to Examples. However, the present invention is not intended to be limited to them by any means.

Example 1

The dissolution rate of compound I from each tablet in the neutral region was compared using varying weights of tablets with the amount of compound I (compound Ia) kept constant.

(1) Tablets containing compound Ia were produced according to the formulations described in Table 1 and examined for dissolution properties at 50 rpm by the second method (paddle method) described in the Japanese Pharmacopoeia. The dissolution amount was calculated as an average percentage dissolution of 6 tablets. The dissolution medium used was phosphate buffer of pH 6.8 (USP Phosphate buffer (pH 6.8)).

Ingredients shown in Table 1, except for hydroxypropyl cellulose and magnesium stearate, were mixed using a polyvinyl bag, and the mixture was granulated by use of aqueous hydroxypropyl cellulose solution. The thus-produced granules were mixed with magnesium stearate, to thereby yield granules which were compressed into tablets (formulation A: 19×7.5 mm, caplets, compression pressure: 12 kN; formulation B: tablet diameter: 9.5 mmφ, round punch and die, compression pressure: 8.5 kN; formulation C: tablet diameter: 8.5 mmφ, round punch and die, compression pressure: 6 kN; and formulation D: tablet diameter: 7.5 mmφ, round punch and die, compression pressure: 4.5 kN). The tablets were designed such that the tablets had the same density (1.25 mg/mm$^3$), to exclude the influence of difference in tablet density on the dissolution properties in the vicinity of the neutral region.

The following were used as the ingredients described in Table 1: D-mannitol (manufactured by Roquette Corp. (trade name: Pearitol 50C) or TOWA-KASEI Co., Ltd. (trade name: Mannit P)) and pregelatinized starch (manufactured by Asahi Kasei Chemicals Corp. (trade name: PCS PC-10)) as excipients, crospovidone (manufactured by ISP (trade name: Polyplasdone INF-10)) as a disintegrant, hydroxypropylcellulose (manufactured by Nippon Soda Co., Ltd. (trade name: HPC-L)) as a binder, and magnesium stearate (manufactured by Tyco Healthcare (trade name: HyQual)) as a lubricant.

TABLE 1

| | | Formulation | | | |
|---|---|---|---|---|---|
| | | A | B | C | D |
| Ingredient (mg) | Compound Ia (in terms of compound I) | 40.4 (30.0) | 40.4 (30.0) | 40.4 (30.0) | 40.4 (30.0) |
| | D-mannitol | 354.4 | 162.4 | 99.2 | 67.3 |
| | Pregelatinized starch | 150.0 | 69.6 | 42.0 | 28.5 |
| | Crospovidone | 32.1 | 16.05 | 10.7 | 8.0 |
| | Hydroxypropylcellulose | 18.3 | 9.15 | 6.1 | 4.6 |
| | Magnesium stearate | 4.8 | 2.4 | 1.6 | 1.2 |
| Tablet weight (mg) | | 600.0 | 300.0 | 200.0 | 150.0 |
| Proportion of compound I in tablet | | 5% | 10% | 15% | 20% |

Figure 1:
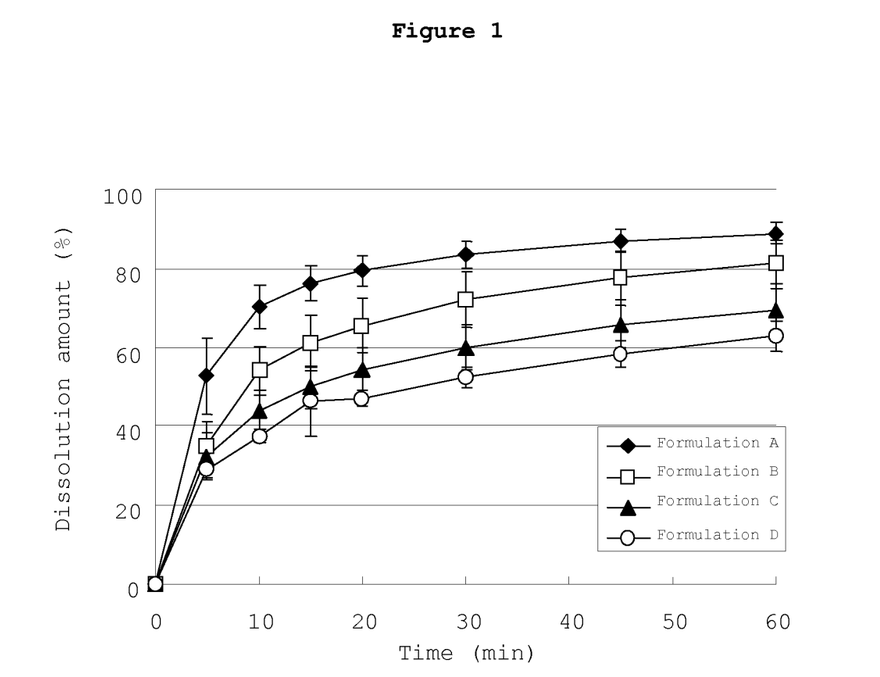
FIG. 1 is a diagram showing the dissolution properties of compound I in the neutral range for tablets having formulations A to D. The vertical axis shows the dissolution amount of compound I, and the horizontal axis shows time (min). The bar in each value represents standard deviation.

FIG. 1 shows results of the dissolution test on the tablets of the formulations shown in Table 1 using the phosphate buffer of pH 6.8.

As a result, it was demonstrated that the lower the proportion of compound I in one tablet becomes, the more the dissolution rate of compound I in the phosphate buffer of pH 6.8 is improved.

(2) A dissolution test was conducted in the same way as in (1) using erythritol instead of D-mannitol and crystalline cellulose instead of pregelatinized starch. As a result, the lower the proportion of compound I in one tablet became, the more the dissolution rate of compound I in the phosphate buffer of pH 6.8 was improved, as with the above test results.

Example 2

Next, the dissolution rate of compound I from each tablet in the neutral region was compared using varying amounts of compound I (compound Ia) with tablet weights kept constant.

Ingredients shown in Table 2, except for hydroxypropyl cellulose and magnesium stearate, were mixed using a polyvinyl bag, and the mixture was granulated by use of aqueous hydroxypropyl cellulose solution. The thus-produced granules were mixed with magnesium stearate, to thereby yield granules which were compressed into tablets (tablet diameter: 9.5 mmφ, round punch and die, compression pressure: 8.5 kN). The tablets were designed such that the tablets had the same density (1.25 mg/mm$^3$), to exclude the influence of difference in tablet density on the dissolution properties in the vicinity of the neutral region. The tablets thus produced were examined for dissolution properties in the same way as in Example 1. In this context, the dissolution amount was calculated as an average percentage dissolution of 6 tablets.

TABLE 2

| | | Formulation | |
|---|---|---|---|
| | | E | B |
| Ingredient (mg) | Compound Ia (in terms of compound I) | 20.2 (15.0) | 40.4 (30.0) |
| | D-mannitol | 177.2 | 162.4 |
| | Pregelatinized starch | 75.0 | 69.6 |
| | Crospovidone | 16.05 | 16.05 |
| | Hydroxypropylcellulose | 9.15 | 9.15 |
| | Magnesium stearate | 2.4 | 2.4 |
| Tablet weight (mg) | | 300.0 | 300.0 |
| Proportion of compound I in tablet | | 5% | 10% |

Figure 2:
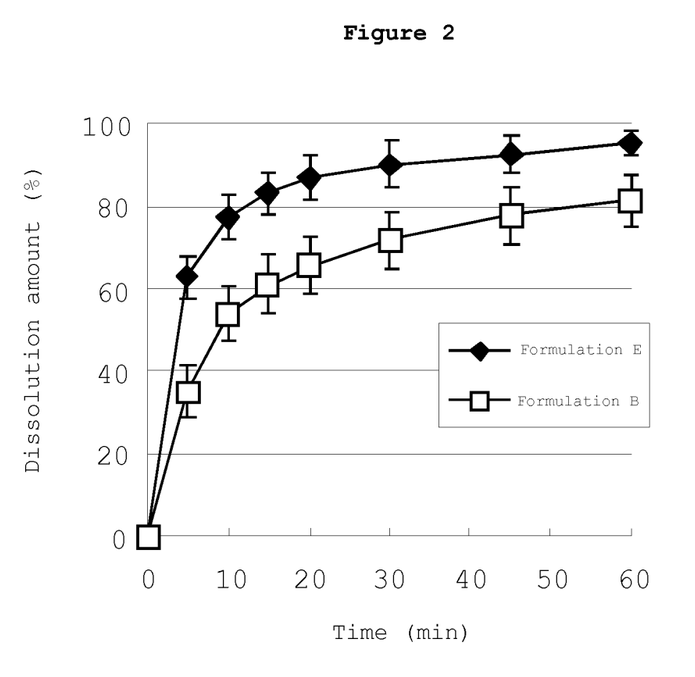
FIG. 2 is a diagram showing the dissolution properties of compound I in the neutral range for tablets having formulations E and B. The vertical axis shows the dissolution amount of compound I, and the horizontal axis shows time (min). The bar in each value represents standard deviation.

FIG. 2 shows results of the dissolution test on the tablets of the formulations shown in Table 2 using the phosphate buffer of pH 6.8.

As a result, it was demonstrated that even in the comparison between the tablets having the same weight and the same shape, the lower the proportion of compound I in one tablet becomes, the more the dissolution rate of compound I in the phosphate buffer of pH 6.8 is improved.

Example 3

Next, the dissolution rate of compound I from each tablet in the neutral region was compared using varying weights of tablets with the proportion of compound I (compound Ia) in the tablet kept constant.

Ingredients shown in Table 3, except for hydroxypropyl cellulose and magnesium stearate, were mixed using a polyvinyl bag, and the mixture was granulated by use of aqueous hydroxypropyl cellulose solution. The thus-produced granules were mixed with magnesium stearate, to thereby yield granules which were compressed into tablets (formulation E: tablet diameter: 9.5 mmφ, round punch and die, compression pressure: 8.5 kN; formulation F: tablet diameter: 6.7 mmφ, round punch and die, compression pressure: 5 kN; and formulation G: 19×7.5 mm, caplets, compression pressure: 12 kN). The tablets were designed such that the tablets had the same density (1.25 mg/mm$^3$), to exclude the influence of difference in tablet density on the dissolution properties in the vicinity of the neutral region. The tablets thus produced were examined for dissolution properties in the same way as in Example 1. In this context, the dissolution amount was calculated as an average percentage dissolution of 6 tablets.

TABLE 3

| | | Formulation | | |
|---|---|---|---|---|
| | | F | E | G |
| Ingredient (mg) | Compound Ia (in terms of compound I) | 6.7 (5.0) | 20.2 (15.0) | 40.4 (30.0) |
| | D-mannitol | 59.1 | 177.2 | 354.4 |
| | pregelatinized starch | 25.0 | 75.0 | 150.0 |
| | Crospovidone | 5.35 | 16.05 | 32.1 |
| | Hydroxypropylcellulose | 3.05 | 9.15 | 18.3 |
| | Magnesium stearate | 0.8 | 2.4 | 4.8 |
| Tablet weight (mg) | | 100.0 | 300.0 | 600.0 |
| Proportion of compound I in tablet | | 5% | 5% | 5% |

Figure 3:
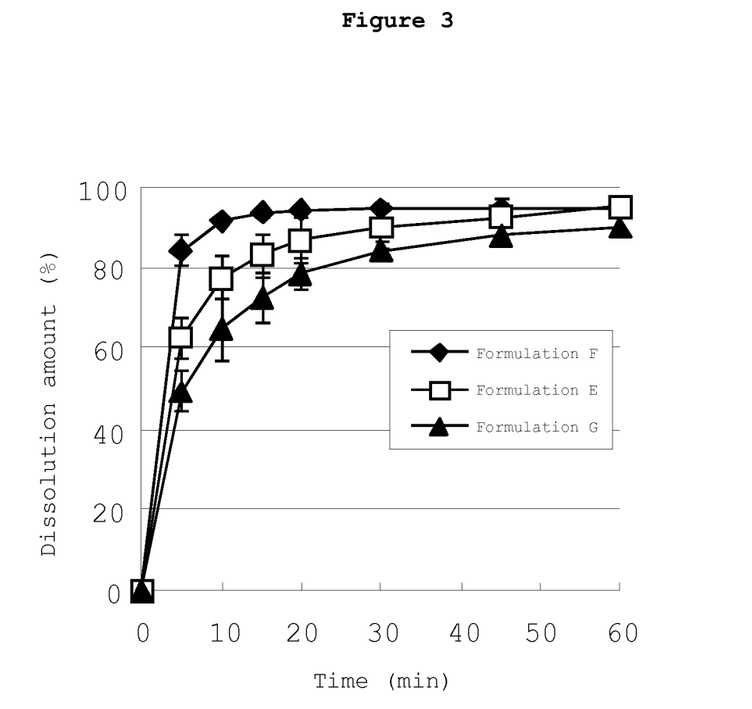
FIG. 3 is a diagram showing the dissolution properties of compound I in the neutral range for tablets having formulations F, E, and G. The vertical axis shows the dissolution amount of compound I, and the horizontal axis shows time (min). The bar in each value represents standard deviation.

FIG. 3 shows results of the dissolution test on the tablets of the formulations shown in Table 3 using the phosphate buffer of pH 6.8.

As a result, when the proportion of compound Ia in each tablet was 6.7% (5% in terms of compound I in each tablet), the tablets having any weight (100 mg, 300 mg, or 600 mg) exhibited favorable dissolution properties. It was also demonstrated that at a constant proportion of compound I in each tablet, the larger the amount of compound I in one tablet becomes, the more dissolution is delayed.

Industrial Applicability

The present invention provides a pharmaceutical composition that is improved in its dissolution properties in the neutral region and is useful as an agent for preventing and/or treating thrombosis or embolism.

The invention claimed is:

1. A solid pharmaceutical composition containing $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide of the following formula (I):

(I)

or a pharmacologically acceptable salt thereof, or a hydrate thereof, wherein the content of the compound of formula (I) is 0.5% by weight or more and less than 10% by weight with respect to the total weight of the pharmaceutical composition.

2. The pharmaceutical composition according to claim 1, wherein the dosage form is a tablet.

3. The pharmaceutical composition according to claim 1, wherein the tablet has a density of 1.2 $mg/mm^3$ to 1.4 $mg/mm^3$.

4. The pharmaceutical composition according to claim 1, wherein the pharmaceutical composition further contains a sugar alcohol and a water-swelling additive as excipients.

5. The pharmaceutical composition according to claim 1, wherein the sugar alcohol is D-mannitol or erythritol, and the water-swelling additive is pregelatinized starch or crystalline cellulose.

6. The pharmaceutical composition according to claim 5, wherein the sugar alcohol is D-mannitol, and the water-swelling additive is pregelatinized starch.

7. The pharmaceutical composition according to claim 1, wherein the coating agents are one or more species selected from the group consisting of a saccharide, hypromellose, methylcellulose, ethylcellulose, hydroxypropyl cellulose, polyvinyl alcohol, povidone, vinyl acetate resin, polyvinyl acetal diethylaminoacetate, aminoalkyl methacrylate copolymer RS, and ethyl acrylate-methyl methacrylate copolymer dispersion.

8. The pharmaceutical composition according to claim 7, wherein the saccharide is selected from the group consisting of sucrose and mannitol.

9. The pharmaceutical composition according to claim 1, wherein the compound of formula (I) or a pharmacologically acceptable salt thereof, or a hydrate thereof is $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate represented by the following formula (Ia):

(Ia)

* * * * *